(12) United States Patent
Hogwood et al.

(10) Patent No.: US 10,994,085 B2
(45) Date of Patent: May 4, 2021

(54) AEROSOL-GENERATING SYSTEM COMPRISING INTEGRATED PIERCING ELEMENT

(71) Applicant: Philip Morris Products S.A., Neuchatel (CH)

(72) Inventors: Jonathan Hogwood, Royston (GB); Stuart Michael Ruan Jones, Royston (GB); John Antony Stephenson, Cambridge (GB); David Edington, St Albans (GB); Christopher Coulson, London (GB)

(73) Assignee: Philip Morris Products S.A., Neuchatel (CH)

( * ) Notice: Subject to any disclaimer, the term of this patent is extended or adjusted under 35 U.S.C. 154(b) by 490 days.

(21) Appl. No.: 15/555,702

(22) PCT Filed: Mar. 24, 2016

(86) PCT No.: PCT/EP2016/056572
§ 371 (c)(1),
(2) Date: Sep. 5, 2017

(87) PCT Pub. No.: WO2016/156212
PCT Pub. Date: Oct. 6, 2016

(65) Prior Publication Data
US 2018/0043113 A1    Feb. 15, 2018

(30) Foreign Application Priority Data

Mar. 27, 2015 (EP) .................................. 15161532

(51) Int. Cl.
*A61M 15/06* (2006.01)
*A24F 47/00* (2020.01)
(Continued)

(52) U.S. Cl.
CPC ........... *A61M 15/06* (2013.01); *A24F 47/008* (2013.01); *A61M 11/042* (2014.02);
(Continued)

(58) Field of Classification Search
CPC .......... A61M 15/06; A61M 11/04–048; A61M 15/0028–0041; A24F 47/00;
(Continued)

(56) References Cited

U.S. PATENT DOCUMENTS

2008/0241255 A1* 10/2008 Rose .................. A61K 31/4439
424/489
2009/0151717 A1* 6/2009 Bowen ................. A61M 11/048
128/200.23
(Continued)

FOREIGN PATENT DOCUMENTS

CN    102612361 A    7/2012
CN    204070540 U    1/2015
(Continued)

OTHER PUBLICATIONS

Japanese Office Action dated Mar. 23, 2020 in Japanese Patent Application No. 2017-546616 (with English translation), 11 pages.
(Continued)

*Primary Examiner* — Kendra D Carter
*Assistant Examiner* — Thao Tran
(74) *Attorney, Agent, or Firm* — Oblon, McClelland, Maier & Neustadt, L.L.P.

(57) ABSTRACT

An aerosol-generating system is provided, including an aerosol-generating device including a heater element, and an aerosol-generating article configured to engage with the aerosol-generating device. The aerosol-generating article includes a medicament source, a volatile delivery enhancing compound source, and at least one frangible barrier sealing the medicament source and the volatile delivery enhancing
(Continued)

compound source. The aerosol-generating system also includes at least one piercing element disposed on one of the aerosol-generating device and the aerosol-generating article, the at least one piercing element being configured to pierce the at least one frangible barrier when activated by a user.

6 Claims, 6 Drawing Sheets

(51) Int. Cl.
*A61M 11/04* (2006.01)
*A61M 15/00* (2006.01)

(52) U.S. Cl.
CPC .... *A61M 15/0021* (2014.02); *A61M 15/0035* (2014.02); *A61M 2205/8206* (2013.01)

(58) Field of Classification Search
CPC .... A24F 47/002; A24F 47/004; A24F 47/006; A24F 47/008
See application file for complete search history.

(56) References Cited

U.S. PATENT DOCUMENTS

| | | | | |
|---|---|---|---|---|
| 2010/0006113 | A1* | 1/2010 | Urtsev | A61M 15/06 131/273 |
| 2012/0204889 | A1* | 8/2012 | Xiu | A24F 47/008 131/273 |
| 2012/0255567 | A1* | 10/2012 | Rose | A61P 3/04 131/273 |
| 2015/0223520 | A1* | 8/2015 | Phillips | A24F 47/006 131/328 |
| 2016/0022930 | A1 | 1/2016 | Greim et al. | |
| 2016/0029694 | A1 | 2/2016 | Clements et al. | |
| 2016/0101245 | A1* | 4/2016 | Hoekman | A61M 15/0035 128/200.23 |
| 2016/0228658 | A1* | 8/2016 | Minskoff | A61M 15/0005 |
| 2017/0215485 | A1* | 8/2017 | Zitzke | A61M 15/008 |

FOREIGN PATENT DOCUMENTS

| | | |
|---|---|---|
| CN | 204070553 U | 1/2015 |
| EP | 2 477 607 A4 | 5/2014 |
| JP | 2010-532672 A | 10/2010 |
| JP | 2010-532682 A | 10/2010 |
| JP | 2013-519382 A | 5/2013 |
| WO | WO 2008/121610 A1 | 10/2008 |
| WO | WO 2011/034723 A1 | 3/2011 |
| WO | WO 2014/140087 A1 | 9/2014 |
| WO | WO 2014/140320 A1 | 9/2014 |
| WO | WO 2014/179228 A1 | 11/2014 |
| WO | WO 2014/187770 A2 | 11/2014 |
| WO | WO 2015/000974 A1 | 1/2015 |
| WO | 2015/040180 A2 | 3/2015 |
| WO | WO 2015/082652 A1 | 6/2015 |

OTHER PUBLICATIONS

International Search Report and Written Opinion dated Jun. 17, 2016 in PCT/EP2016/056572, filed Mar. 24, 2016.
Combined Chinese Office Action and Search Report dated Oct. 26, 2020 in Patent Application No. 201680017139.4 (with English language translation), 13 pages.

* cited by examiner

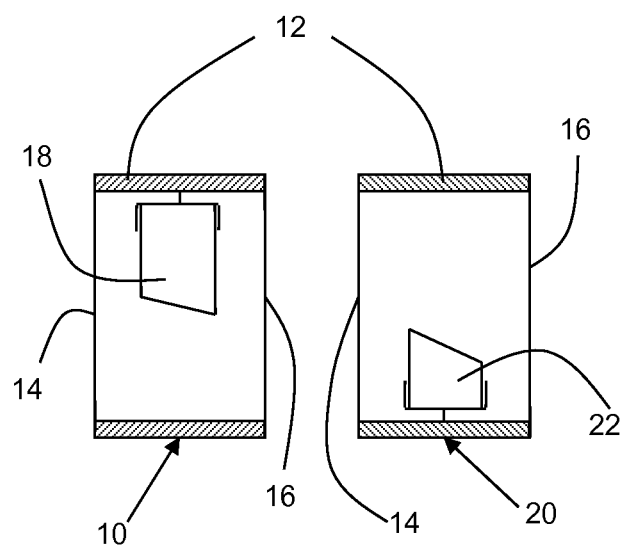
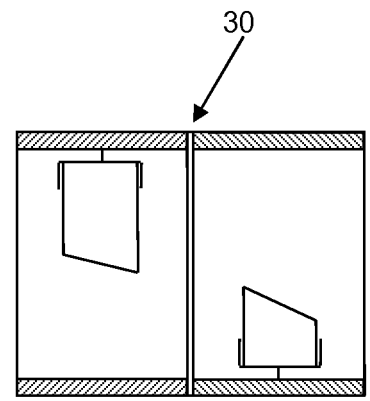
Figure 1
Figure 2
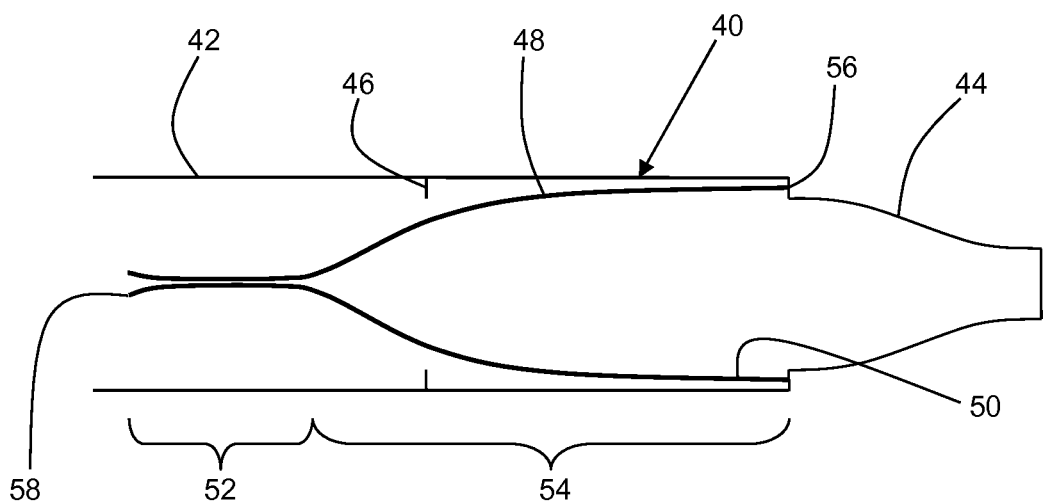
Figure 3

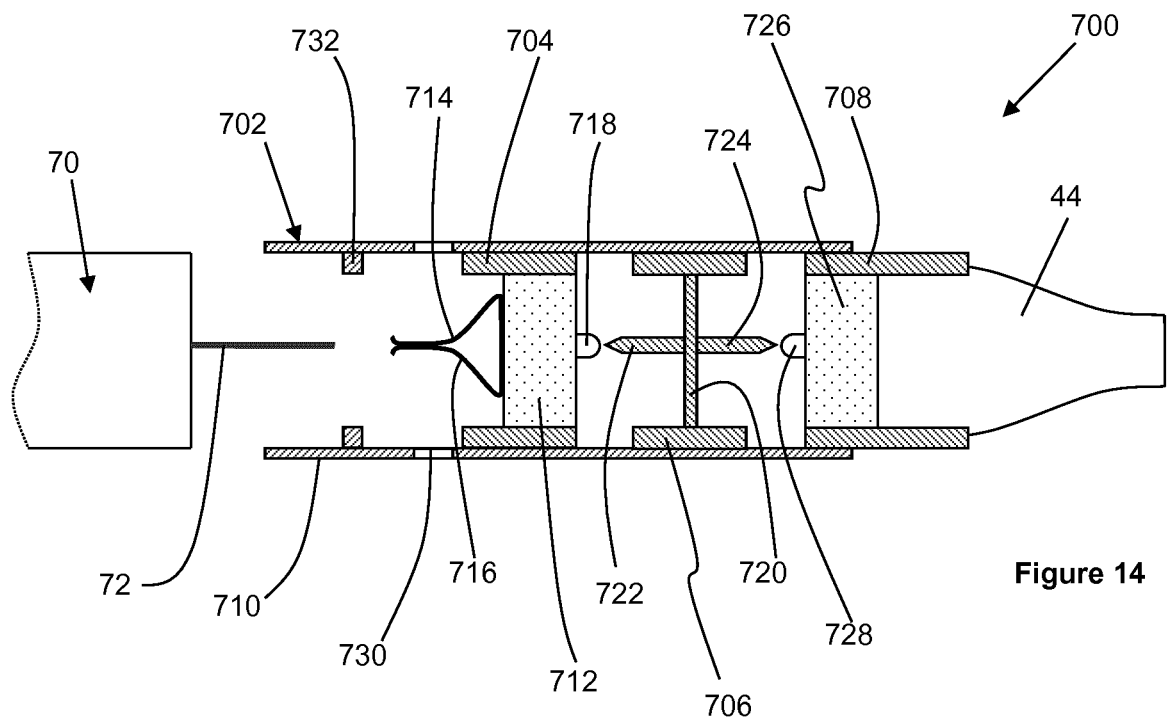
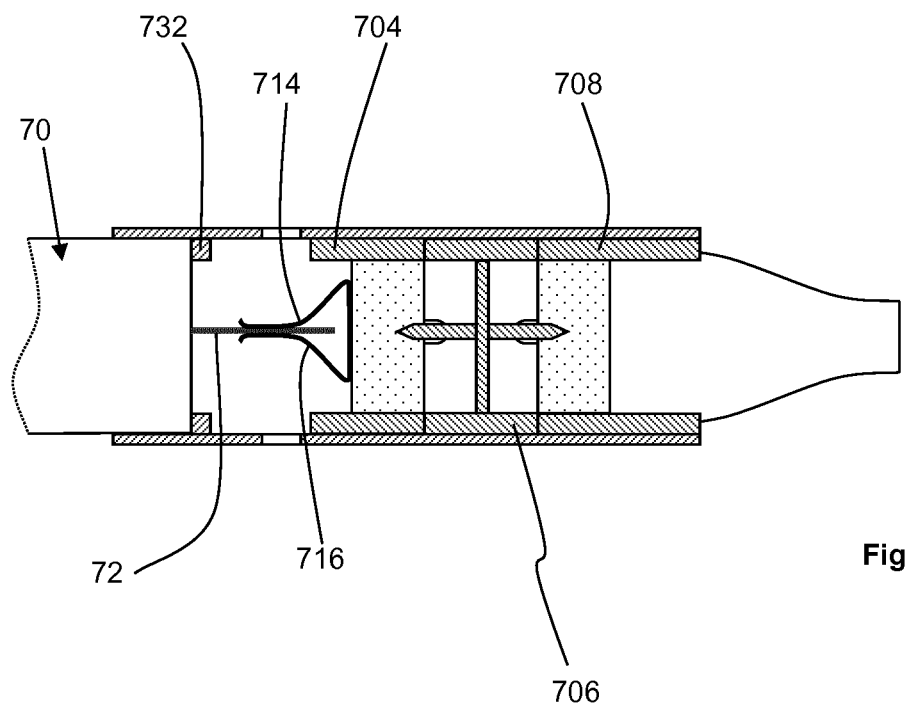
Figure 14
Figure 15

AEROSOL-GENERATING SYSTEM COMPRISING INTEGRATED PIERCING ELEMENT

The present invention relates to an aerosol-generating system for generating an aerosol comprising a medicament. The invention finds particular application as an aerosol-generating system for generating an aerosol comprising nicotine salt particles.

Some devices for delivering nicotine or other medicaments to a user comprise a volatile acid, such as pyruvic acid, or other volatile delivery enhancing compound source and a nicotine or other medicament source. The volatile delivery enhancing compound is reacted with nicotine in the gas phase to form an aerosol of nicotine salt particles that is inhaled by the user.

At room temperature pyruvic acid and nicotine are both sufficiently volatile to form respective vapours that react with one another in the gas phase to form nicotine pyruvate salt particles. Therefore, to prevent premature evaporation of the volatile delivery enhancing compound and the nicotine both sources are usually sealed with one or more frangible seals that a user must break to use the aerosol-generating system. However, it may be difficult to provide a frangible seal that can be reliably and consistently broken by a user to provide a consistent user experience. Accordingly, it would be desirable to provide a device comprising nicotine or other medicament source and a volatile delivery enhancing compound source that overcomes these difficulties.

The present invention provides an aerosol-generating system comprising an aerosol-generating device comprising a heater element, and an aerosol-generating article configured to engage with the aerosol-generating device. The aerosol-generating article comprises a medicament source, a volatile delivery enhancing compound source, and at least one frangible barrier sealing the medicament source and the volatile delivery enhancing compound source. The aerosol-generating system also comprises at least one piercing element provided on one of the aerosol-generating device and the aerosol-generating article, wherein the at least one piercing element is arranged to pierce the at least one frangible barrier when activated by a user.

As used herein, the term "aerosol-generating device" refers to a device that interacts with an aerosol-generating article to generate an aerosol that is directly inhalable into a user's lungs thorough the user's mouth.

As used herein, the term "aerosol-generating article" refers to an article comprising an aerosol-forming substrate capable of releasing volatile compounds, which can form an aerosol. The aerosol-generating article may comprise an aerosol-forming substrate capable of releasing upon heating volatile compounds, which can form an aerosol. An aerosol-generating article may be entirely consumable and mainly comprise a medicament source and a volatile delivery enhancing compound. An aerosol-generating article may comprise a reusable portion, such as a mouthpiece configured for attachment to an aerosol-generating device, and a consumable portion comprising the medicament and volatile delivery enhancing compound sources and configured for insertion into the reusable portion.

As used herein, the term "aerosol-generating system" refers to a combination of an aerosol-generating article with an aerosol-generating device.

As used herein, the term "medicament source" refers to a source of one or more volatile compounds intended for delivery to the lungs of a user. In preferred embodiments, the medicament source comprises a nicotine source.

As used herein, the term "volatile delivery enhancing compound source" refers to a source of one or more volatile compounds that react with the medicament source in the gas phase to aid delivery of the one or more compounds from the medicament source to the user.

By providing at least one integrated piercing element on one of the aerosol-generating device and the aerosol-generating article, an aerosol-generating system in accordance with the present invention may provide a convenient and reliable means for a user to consistently break the at least one frangible barrier prior to using the aerosol-generating system.

The aerosol-generating article may comprise a tubular portion housing the medicament source and the volatile delivery enhancing compound source, and the at least one frangible barrier may comprise at least one frangible barrier extending across at least one end of the tubular portion. The at least one frangible barrier may comprise a foil or film.

The aerosol-generating article may further comprise a mouthpiece portion, the mouthpiece portion housing the at least one piercing element and configured to receive the tubular portion within the mouthpiece portion, wherein the at least one piercing element comprises at least one resilient member arranged to pierce the at least one frangible barrier when the tubular portion is inserted into the mouthpiece portion. As used herein, the term "resilient member" refers to a part of the aerosol-generating system that resists movement or deformation upon application of a force to the resilient member. Once an applied force is removed a resilient member will at least partially return to its position or shape prior to the application of the force. The resilient member may comprise an elongate metal plate or blade. By housing the resilient member within a mouthpiece portion into which the tubular portion is inserted, the resilient member can provide reliable and consistent rupturing of the at least one frangible barrier.

In those embodiments comprising a resilient member provided within a mouthpiece portion, the heater element of the aerosol-generating device may be an elongate heater element comprising a proximal end attached to the aerosol-generating device and a free distal end for insertion into the aerosol-generating article. The at least one resilient member may be arranged so that the at least one resilient member is resiliently biased against the heater element when the aerosol-generating article is engaged with the aerosol-generating device. The at least one resilient member is formed from a resilient material that can withstand the operating temperature of the heater element. The at least one resilient member may be formed from a metal. The at least one resilient member can be used to conduct heat from the heater element to at least one of the medicament source and the volatile delivery enhancing compound source.

The at least one resilient member may comprise first and second resilient members configured so that each resilient member is resiliently biased against the heater element when the aerosol-generating article is engaged with the aerosol-generating device so that the heater element is positioned between the first and second resilient members.

As an alternative to providing a resilient member to pierce the at least one frangible barrier, the heater element may be an elongate heater element comprising a proximal end attached to the aerosol-generating device and a free distal end for insertion into the aerosol-generating article, and wherein the elongate heater element forms the at least one piercing element so that the elongate heater element pierces the at least one frangible barrier on the tubular portion when a user engages the aerosol-generating article with the aerosol-generating device. Advantageously, such embodiments eliminate the need for a separate piercing element.

As a further alternative to any of the embodiments described above, the at least one piercing element may be provided on a wall of the aerosol-generating article, and wherein the medicament source and the volatile delivery enhancing compound source are moveable relative to the at least one piercing element. The at least one frangible barrier comprises a first frangible barrier sealing the medicament source and a second frangible barrier sealing the volatile delivery enhancing compound source. The at least one piercing element comprises a first piercing element provided on the wall of the aerosol-generating article adjacent the medicament source and a second piercing element provided on the wall of the aerosol-generating article adjacent the volatile delivery enhancing compound source.

In those embodiments in which the at least one piercing element is provided on a wall of the aerosol-generating article, the aerosol-generating system may comprise at least one resilient member provided inside the aerosol-generating article, wherein the medicament source and the volatile delivery enhancing compound source are provided on the at least one resilient member. The at least one resilient member is arranged so that movement of the at least one resilient member towards the at least one piercing element allows the at least one piercing element to pierce the at least one frangible barrier.

The at least one piercing element may be provided on a first wall of the aerosol-generating article, and the medicament source and the volatile delivery enhancing compound source may be provided on a second wall of the aerosol-generating article. The first and second walls of the aerosol-generating article are moveable relative to each other so that relative movement between the first and second walls allows the at least one piercing element to pierce the at least one frangible barrier.

The aerosol-generating article may comprising a housing and an upstream member received within the housing, wherein one of the medicament source or the volatile delivery enhancing compound source is provided on a downstream end of the upstream member. A piercing member may be slidably received within the housing and downstream of the upstream member. The at least one piercing element may comprise a first piercing element provided on an upstream end of the piercing member and a second piercing element provided on a downstream end of the piercing member. A downstream member is received within the housing and downstream of the piercing member, wherein one of the volatile delivery enhancing compound source or the medicament source is provided on an upstream end of the downstream member. The at least one frangible barrier may comprise a first frangible barrier sealing the medicament source and a second frangible barrier sealing the volatile delivery enhancing compound source. One of the upstream member or the downstream member may be slidably received within the housing so that relative sliding movement between the upstream member, the piercing member and the downstream member allows the first and second piercing elements to pierce the first and second frangible barriers.

In any of the embodiments described above, the medicament source and the volatile delivery enhancing compound source may comprise a liquid sorbed onto a sorption element. The at least one frangible barrier may be formed from a sheet material wrapped around one or both of the sources, or extending across an opening in aerosol-generating article. The sheet material may be formed from a metal foil or film, for example.

The medicament and the volatile delivery enhancing compound may each comprise a liquid containing with a blister, wherein the blisters form the medicament source and the volatile delivery enhancing compound source. Each blister may be formed from a non-permeable material, such as a plastic, and each blister forms a frangible barrier sealing the medicament or the volatile delivery enhancing compound.

In any of the embodiments described above, the at least one piercing element may have any suitable shape and form for piercing the at least one frangible barrier. The at least one piercing element may comprise an elongate element such as a spike or blade.

The at least one piercing element may be formed from any suitable material. Preferably, the at least one piercing element is formed from a rigid material, such as a plastic or a metal. Preferably, the at least one piercing element is sufficiently rigid such that it can pierce the at least one frangible barrier with substantially no deformation of the at least one piercing element.

The medicament source and the volatile delivery enhancing compound source are preferably arranged in series within the aerosol-generating article.

As used herein, by "series" it is meant that the medicament source and the volatile delivery enhancing compound source are arranged within the aerosol-generating article so that in use an air stream drawn through the aerosol-generating article passes through one of the medicament source and the volatile delivery enhancing compound source and then passes through the other of the medicament source and the volatile delivery enhancing compound source.

Preferably, the medicament source is upstream of the volatile delivery enhancing compound source so that in use medicament vapour is released from the medicament source into the air stream drawn through the aerosol-generating article and volatile delivery enhancing compound vapour is released from the volatile delivery enhancing compound source into the medicament-containing air stream drawn through the aerosol-generating article. The medicament vapour reacts with the volatile delivery enhancing compound vapour in the gas phase to form an aerosol, which is delivered to a user.

The medicament source and the volatile delivery enhancing compound source may be arranged in parallel within the aerosol-generating article.

The volatile delivery enhancing compound preferably has a vapour pressure of at least about 20 Pa, more preferably at least about 50 Pa, more preferably at least about 75 Pa, most preferably at least 100 Pa. Unless otherwise stated, all vapour pressures referred to herein are vapour pressures at 25° C. measured in accordance with ASTM E1194-07.

Preferably, the volatile delivery enhancing compound has a vapour pressure of less than or equal to about 400 Pa, more preferably less than or equal to about 300 Pa, even more preferably less than or equal to about 275 Pa, most preferably less than or equal to about 250 Pa at 25° C.

The volatile delivery enhancing compound may have a vapour pressure of between about 20 Pa and about 400 Pa, more preferably between about 20 Pa and about 300 Pa, even more preferably between about 20 Pa and about 275 Pa, most preferably between about 20 Pa and about 250 Pa at 25° C.

The volatile delivery enhancing compound may have a vapour pressure of between about 50 Pa and about 400 Pa, more preferably between about 50 Pa and about 300 Pa, even more preferably between about 50 Pa and about 275 Pa, most preferably between about 50 Pa and about 250 Pa at 25° C.

The volatile delivery enhancing compound may have a vapour pressure of between about 75 Pa and about 400 Pa, more preferably between about 75 Pa and about 300 Pa, even more preferably between about 75 Pa and about 275 Pa, most preferably between about 75 Pa and about 250 Pa at 25° C.

The volatile delivery enhancing compound may have a vapour pressure of between about 100 Pa and about 400 Pa, more preferably between about 100 Pa and about 300 Pa, even more preferably between about 100 Pa and about 275 Pa, most preferably between about 100 Pa and about 250 Pa at 25° C.

The volatile delivery enhancing compound may comprise a single compound. The volatile delivery enhancing compound may comprise two or more different compounds.

Where the volatile delivery enhancing compound comprises two or more different compounds, the two or more different compounds in combination have a vapour pressure of at least about 20 Pa at 25° C.

Preferably, the volatile delivery enhancing compound is a volatile liquid.

The volatile delivery enhancing compound may comprise a mixture of two or more different liquid compounds.

The volatile delivery enhancing compound may comprise an aqueous solution of one or more compounds. The volatile delivery enhancing compound may comprise a non-aqueous solution of one or more compounds.

The volatile delivery enhancing compound may comprise two or more different volatile compounds. The volatile delivery enhancing compound may comprise a mixture of two or more different volatile liquid compounds.

The volatile delivery enhancing compound may comprise one or more non-volatile compounds and one or more volatile compounds. The volatile delivery enhancing compound may comprise a solution of one or more non-volatile compounds in a volatile solvent or a mixture of one or more non-volatile liquid compounds and one or more volatile liquid compounds.

Preferably, the volatile delivery enhancing compound comprises an acid. The volatile delivery enhancing compound may comprise an organic acid or an inorganic acid. Preferably, the volatile delivery enhancing compound comprises an organic acid, more preferably a carboxylic acid, most preferably an alpha-keto or 2-oxo acid. The volatile delivery enhancing compound may comprise lactic acid. Other suitable acids includes aspartic acid, glutamic acid, salicylic acid, tartaric acid, gallic acid, levulinic acid, acetic acid, malic acid, citric acid, oxalic acid, sulphuric acid, palmitic acid, and alginic acid. Preferably, the volatile delivery enhancing compound comprises an acid selected from the group consisting of 3-methyl-2-oxopentanoic acid, pyruvic acid, 2-oxopentanoic acid, 4-methyl-2-oxopentanoic acid, 3-methyl-2-oxobutanoic acid, 2-oxooctanoic acid and combinations thereof. Preferably, the volatile delivery enhancing compound comprises pyruvic acid.

Preferably, the volatile delivery enhancing compound source comprises a sorption element and a volatile delivery enhancing compound sorbed on the sorption element. The volatile delivery enhancing compound may be sorbed onto the sorption element during manufacture and the sorption element may be sealed. The volatile delivery enhancing compound may be stored separately from the sorption element, for example in a blister on or adjacent the sorption element.

As used herein, by "sorbed" it is meant that the volatile delivery enhancing compound is adsorbed on the surface of the sorption element, or absorbed in the sorption element, or both adsorbed on and absorbed in the sorption element. Preferably, the volatile delivery enhancing compound is adsorbed on the sorption element.

The sorption element may be formed from any suitable material or combination of materials. For example, the sorption element may comprise one or more of glass, stainless steel, aluminium, polyethylene (PE), polypropylene, polyethylene terephthalate (PET), polybutylene terephthalate (PBT), polytetrafluoroethylene (PTFE), expanded polytetrafluoroethylene (ePTFE), and BAREX®.

In a preferred embodiment, the sorption element is a porous sorption element.

The sorption element may be a porous sorption element comprising one or more materials selected from the group consisting of porous plastic materials, porous polymer fibres and porous glass fibres.

The sorption element is preferably chemically inert with respect to the volatile delivery enhancing compound.

The sorption element may have any suitable size and shape.

The size, shape and composition of the sorption element may be chosen to allow a desired amount of volatile delivery enhancing compound to be sorbed on the sorption element.

Preferably, between about 20 μl and about 200 μl, more preferably between about 40 μl and about 150 μl, most preferably between about 50 μl and about 100 μl of the volatile delivery enhancing compound is sorbed on the sorption element.

The sorption element advantageously acts as a reservoir for the volatile delivery enhancing compound.

Preferably, the medicament has a melting point below about 150 degrees Celsius.

Alternatively or in addition, preferably the medicament has a boiling point below about 300 degrees Celsius.

In certain preferred embodiments, the medicament comprises one or more aliphatic or aromatic, saturated or unsaturated nitrogenous bases (nitrogen containing alkaline compounds) in which a nitrogen atom is present in a heterocyclic ring or in an acyclic chain (substitution).

The medicament may comprise one or more compounds selected from the group consisting of: nicotine; 7-Hydroxymitragynine; Arecoline; Atropine; Bupropion; Cathine (D-norpseudoephedrine); Chlorpheneramine; Dibucaine; Dimemorphan, Dimethyltryptamine, Diphenhydramine, Ephedrine, Hordenine, Hyoscyamine, Isoarecoline, Levorphanol, Lobeline, Mesembrine, Mitragynine, Muscatine, Procaine, Pseudo ephedrine, Pyrilamine, Raclopride, Ritodrine, Scopolamine, Sparteine (Lupinidine) and Ticlopidine; tobacco smoke constituents, such as 1,2,3,4 Tetrahydroisoquinolines, Anabasine, Anatabine, Cotinine, Myosmine, Nicotrine, Norcotinine, and Nornicotine; anti-asthmatic drugs, such as Orciprenaline, Propranolol and Terbutaline; anti-angina drugs, such as Nicorandil, Oxprenolol and Verapamil; antiarrhythmic drugs, such as Lidocaine; nicotinic agonists, such as Epibatidine, 5-(2R)-azetidinylmethoxy)-2-chloropyridine (ABT-594), (S)-3-methyl-5-(1-methyl-2-pyrrolidinyl)isoxazole (ABT 418) and (±)-2-(3-Pyridinyl)-1-azabicyclo[2.2.2]octane (RJR-2429); nicotinic antagonists, such as Methyllycacotinine and Mecamylamine; acetyl cholinesterase inhibitors, such as Galantamine, Pyridostigmine, Physostigmine and Tacrine; and MAO-inhibitors, such as Methoxy-N,N-dimethyltryptamine, 5-methoxy-α-methyltryptamine, Alpha-methyltryptamine, Iproclozide, Iproniazide, Isocarboxazide, Linezolid, Meclobemide, N,N-Dimethyltryptamine, Phenelzine, Phenyl ethylamine, Toloxatone, Tranylcypromine and Tryptamine.

Preferably, the medicament source comprises a nicotine source. The nicotine source may comprise one or more of nicotine, nicotine base, a nicotine salt, such as nicotine-HCl, nicotine-bitartrate, or nicotine-tartrate, or a nicotine derivative.

The nicotine source may comprise natural nicotine or synthetic nicotine.

The nicotine source may comprise pure nicotine, a solution of nicotine in an aqueous or non-aqueous solvent or a liquid tobacco extract.

The nicotine source may further comprise an electrolyte forming compound. The electrolyte forming compound may be selected from the group consisting of alkali metal hydroxides, alkali metal oxides, alkali metal salts, alkaline earth metal oxides, alkaline earth metal hydroxides and combinations thereof.

The nicotine source may comprise an electrolyte forming compound selected from the group consisting of potassium hydroxide, sodium hydroxide, lithium oxide, barium oxide, potassium chloride, sodium chloride, sodium carbonate, sodium citrate, ammonium sulfate and combinations thereof.

The nicotine source may comprise an aqueous solution of nicotine, nicotine base, a nicotine salt or a nicotine derivative and an electrolyte forming compound.

The nicotine source may further comprise other components including, but not limited to, natural flavours, artificial flavours and antioxidants.

The medicament source may comprise a sorption element as described above and a medicament sorbed on the sorption element. The medicament may be sorbed onto the sorption element during manufacture and the sorption element may be sealed. The medicament may be stored separately from the sorption element, for example in a blister on or adjacent the sorption element.

The aerosol-generating device may be configured to heat the medicament source and the volatile delivery enhancing compound source of the aerosol-generating article so that the medicament source of the aerosol-generating article has a higher temperature than the volatile delivery enhancing compound source of the aerosol-generating article. The aerosol-generating device may be configured to substantially simultaneously heat the medicament source and the volatile delivery enhancing compound source of the aerosol-generating article.

In any of the embodiments described above, the aerosol-generating device and the aerosol-generating article may be configured to heat the medicament source to a first temperature and to heat the volatile delivery enhancing compound source to a second temperature, wherein the first temperature is at least about 50 degrees Celsius higher than the second temperature, preferably at least about 70 degrees Celsius higher than the second temperature, most preferably at least about 80 degrees Celsius higher than the second temperature. Additionally, or alternatively, the first temperature is preferably no more than about 100 degrees Celsius higher than the second temperature. Preferably, the temperature difference between the first and second temperatures is between about 50 and about 100 degrees Celsius, more preferably between about 60 and about 100 degrees Celsius, most preferably between about 80 and about 100 degrees Celsius.

In any of the embodiments described above, the aerosol-generating device and the aerosol-generating article may be configured to heat the volatile delivery enhancing compound source to a temperature of at least about 30 degrees Celsius. Additionally, or alternatively, the aerosol-generating device and the aerosol-generating article may be configured to heat the volatile delivery enhancing compound source to a temperature of less than about 100 degrees Celsius, preferably less than about 70 degrees Celsius. Preferably, the aerosol-generating device and the aerosol-generating article are configured to heat the volatile delivery enhancing compound source to a temperature of between about 30 and about 100 degrees Celsius, more preferably between about 30 and about 70 degrees Celsius.

In any of the embodiments described above, the aerosol-generating device and the aerosol-generating article may be configured to heat the medicament compound source to a temperature of at least about 50 degrees Celsius. Additionally, or alternatively, the aerosol-generating device and the aerosol-generating article may be configured to heat the medicament source to a temperature of less than about 150 degrees Celsius, preferably less than about 100 degrees Celsius. Preferably, the aerosol-generating device and the aerosol-generating article are configured to heat the medicament source to a temperature of between about 50 and about 150 degrees Celsius, more preferably between about 50 and about 100 degrees Celsius.

The aerosol-generating device may further comprise a controller configured to control a supply of power to the heater element.

The aerosol-generating device may further comprise a power supply for supplying power to the heater element and a controller configured to control a supply of power from the power supply to the heater element. The controller of the aerosol-generating device may be configured to control a supply of power from an external power supply to the heater element.

The heater element may be an electric heater element powered by an electric power supply. Where the heater element is an electric heater element, the aerosol-generating device may further comprise an electric power supply and a controller comprising electronic circuitry configured to control the supply of electric power from the electric power supply to the electric heater element.

The power supply may be a DC voltage source. Preferably, the power supply is a battery. The power supply may be a Nickel-metal hydride battery, a Nickel cadmium battery, or a Lithium based battery, for example a Lithium-Cobalt, a Lithium-Iron-Phosphate or a Lithium-Polymer battery. The power supply may be another form of charge storage device such as a capacitor. The power supply may require recharging and may have a capacity that allows for the storage of enough energy for use of the aerosol-generating device with one or more aerosol-generating articles.

The heater element may be a non-electric heater, such as a chemical heating means.

The heater element of the aerosol-generating device preferably comprises a single heater element to simplify the construction of the aerosol-generating device. Differential heating of the medicament source and the volatile delivery enhancing compound source may be achieved by contacting at least one of the sources with the resilient member, which in turn is biased against the heater element.

The heater element may have any suitable shape. Preferably, the heater element is an elongate heater element. In a particularly preferred embodiment, the elongate heater element has a width that is greater than the thickness of the heater element so that the heater element forms a heater blade.

Preferably, the heater element is heated electrically. However, other heating schemes may be used to heat the heater element. The heater element may be heated by conduction from another heat source. The heater element may comprise an infra-red heater element, a photonic source, or an inductive heater element.

The heater element may comprise a heat sink, or heat reservoir comprising a material capable of absorbing and storing heat and subsequently releasing the heat over time to the aerosol-forming article. The heat sink may be formed of any suitable material, such as a suitable metal or ceramic material. Preferably, the material has a high heat capacity (sensible heat storage material), or is a material capable of absorbing and subsequently releasing heat via a reversible process, such as a high temperature phase change. Suitable sensible heat storage materials include silica gel, alumina, carbon, glass mat, glass fibre, minerals, a metal or alloy such as aluminium, silver or lead, and a cellulose material such as paper. Other suitable materials which release heat via a reversible phase change include paraffin, sodium acetate, naphthalene, wax, polyethylene oxide, a metal, a metal salt, a mixture of eutectic salts or an alloy.

Preferably the heater element comprises an electrically resistive material. The heater element may comprise a non-elastic material, for example a ceramic sintered material, such as alumina ($Al_2O_3$) and silicon nitride ($Si_3N_4$), or printed circuit board or silicon rubber. The heater element may comprise an elastic, metallic material, for example an iron alloy or a nickel-chromium alloy.

Other suitable electrically resistive materials include but are not limited to: semiconductors such as doped ceramics, electrically "conductive" ceramics (such as, for example, molybdenum disilicide), carbon, graphite, metals, metal alloys and composite materials made of a ceramic material and a metallic material. Such composite materials may comprise doped or undoped ceramics. Examples of suitable doped ceramics include doped silicon carbides. Examples of suitable metals include titanium, zirconium, tantalum and metals from the platinum group. Examples of suitable metal alloys include stainless steel, nickel-, cobalt-, chromium-, aluminium- titanium- zirconium-, hafnium-, niobium-, molybdenum-, tantalum-, tungsten-, tin-, gallium- and manganese-alloys, and super-alloys based on nickel, iron, cobalt, stainless steel, Timetal® and iron-manganese-aluminium based alloys. Timetal® is a registered trade mark of Titanium Metals Corporation, 1999 Broadway Suite 4300, Denver, Colo. In composite materials, the electrically resistive material may optionally be embedded in, encapsulated or coated with an insulating material or vice-versa, depending on the kinetics of energy transfer and the external physicochemical properties required.

The aerosol-generating device may comprise one or more temperature sensors configured to sense the temperature of at least one of the heater element, the medicament source and the volatile delivery enhancing compound source. The controller may be configured to control a supply of power to the heater element based on the sensed temperature.

The heater element may be formed using a metal having a defined relationship between temperature and resistivity. The metal may be formed as a track between two layers of suitable insulating materials. A heater element formed in this manner may be used both as a heater and a temperature sensor.

The invention will now be further described, by way of example only, with reference to the accompanying drawings in which:

FIGS. 1 and 2 show consumable portions of an aerosol-generating article in accordance with a first embodiment of the present invention;

FIG. 3 shows a reusable portion of an aerosol-generating article in accordance with the first embodiment of the present invention;

Figure 4:
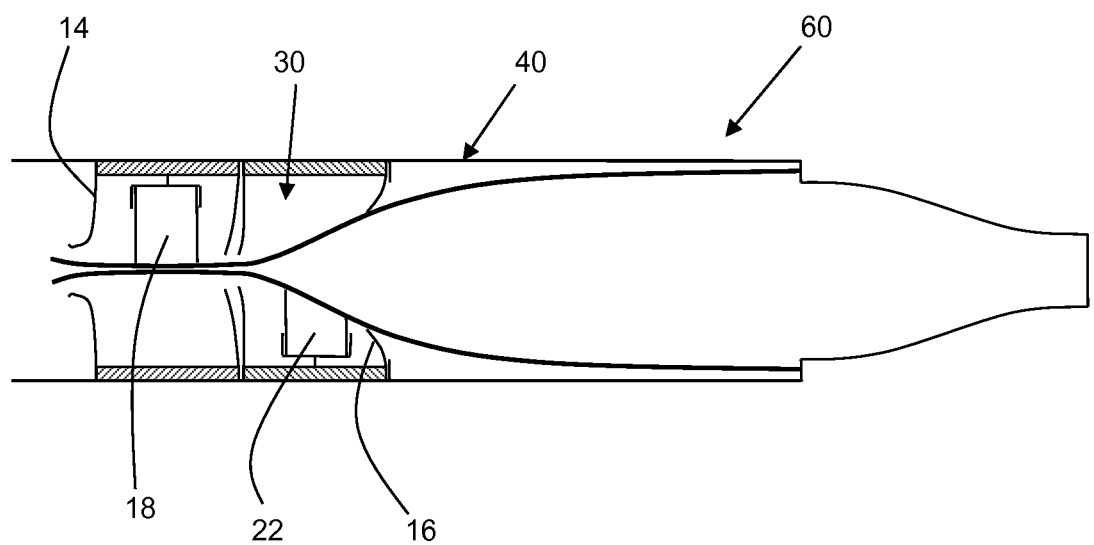
FIG. 4 shows the consumable portions of FIGS. 1 and 2 combined with the reusable portion of FIG. 3 to form an aerosol-generating article in accordance with the first embodiment of the present invention.

FIG. 14 shows an aerosol-generating system in accordance with an fifth embodiment of the present invention, before activation of the aerosol-generating article and before full insertion of the aerosol-generating device into the aerosol-generating article; and FIG. 15 shows the aerosol-generating system of FIG. 14 after activation of the aerosol-generating article and after full insertion of the aerosol-generating device into the aerosol-generating article.

Like reference numerals will be used to designate like parts in the following description of the drawings.

FIG. 1 shows first and second consumable portions of an aerosol-generating article according to a first embodiment of the present invention. First consumable portion 10 comprises a tubular segment 12 sealed at both ends by frangible barriers 14 and 16 formed from a metal foil. A medicament source 18 is mounted on an inner surface of the tubular segment 12 and comprises a medicament, such as nicotine, sorbed on a porous sorption element.

Similarly, the second consumable portion 20 comprises a tubular segment 12 sealed at both ends by frangible barriers 14 and 16. A volatile delivery enhancing compound source 22 is mounted on an inner surface of the tubular segment 12 and comprises a volatile delivery enhancing compound, such as pyruvic acid, sorbed on a porous sorption element.

As shown in FIG. 2, the first and second consumable portions 10 and 20 are secured together to form a consumable 30 that is inserted into a reusable portion of the aerosol-generating article. The first and second consumable portions can be secured together using any suitable means, such as an interference fit between the ends of the tubular segments 12.

FIG. 3 shows the reusable portion 40 of the aerosol-generating article, the reusable portion comprising a tubular outer housing 42 and a mouthpiece 44 at the downstream end of the outer housing 42. The mouthpiece 44 may be formed integrally with the outer housing 42, or the mouthpiece 44 may be formed separately and secured to the upstream end of the outer housing 42, for example using an interference fit. The outer housing 42 and the mouthpiece 44 are formed from a rigid, thermally insulating material, such as a plastic.

The upstream end of the outer housing 42 is open to receive the consumable 30, and stops 46 are provided on an inner surface of the outer housing 42 to limit the insertion of the consumable 30 into the reusable portion 40.

Provided in the outer housing 42 are a pair of opposed resilient members 48 and 50. The resilient member 48 and 50 are shaped so that together they form a "wishbone" shape comprising upstream portions 52 positioned adjacent each other and downstream portions 54 spaced apart from each other. Each resilient member is secured at its downstream end 56 to the outer housing 42. The upstream ends 58 of the resilient members 48 and 50 are curved away from each other to provide a "mouth" to facilitate insertion of a heater element between the upstream portions 52 of the resilient members. The resilient members 48 and 50 are formed from a thermally conductive resilient material, such as a metal, capable of withstanding the operating temperature of the heater element when inserted between the upstream portions 52 of the resilient members.

FIG. 4 shows the consumable 30 inserted into the reusable portion 40 to form the aerosol-generating article 60 according to the first embodiment of the invention. Upon inserting the consumable 30 into the upstream end of the outer housing 42, the resilient members 48 and 50 function as piercing elements and rupture the frangible barriers 14 and 16 sealing the first and second consumable portions 10 and 20, therefore allowing air to flow into the upstream end of the outer housing 42, through the consumable 30, around the resilient members 48 and 50 and out of the aerosol-generating article 60 through the mouthpiece 44.

The consumable 30 is inserted into the upstream end of the outer housing 42 until the downstream end of the consumable 30 abuts the stops 46. At this point, the consumable 30 is fully inserted into the reusable portion 40 so that the medicament source 18 contacts the upstream portion 52 of the first resilient member 48 and the volatile delivery enhancing compound source 22 contacts the downstream portion 54 of the second resilient member 50.

Figure 5:
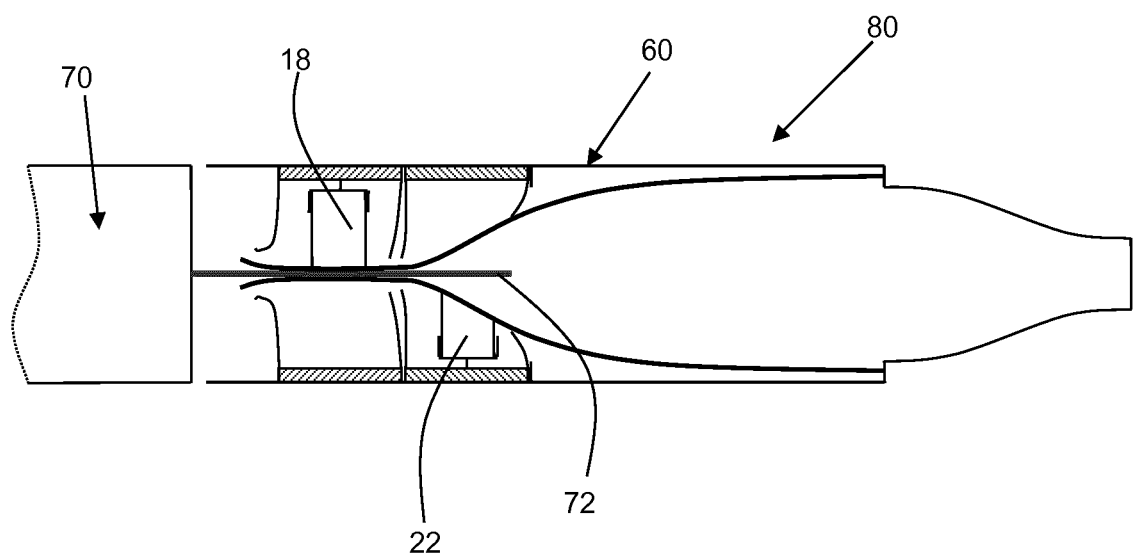
FIG. 5 shows an aerosol-generating device combined with the aerosol-generating article of FIG. 4 to form an aerosol-generating system in accordance with the first embodiment of the present invention.

FIG. 5 shows an aerosol-generating device 70 combined with the aerosol-generating article 60 to form the aerosol-generating system 80 according to the first embodiment of the invention. The aerosol-generating device 70 comprises heater element 72 in the form of a heater blade received between the upstream portions 52 of the resilient members 48 50, which are resiliently biased against the heater element 72. The heater element 72 is electrically heated and the aerosol-generating device may comprise a power source and control electronics, as is known in the art. During operation of the aerosol-generating system 80, the heater element 72 heats the medicament source 18 and the volatile delivery enhancing compound source 22. The medicament source 18 contacts the upstream portion 52 of the first resilient member 48, which directly contacts the heater element 72, whereas the volatile delivery enhancing compound source 22 contacts the downstream portion 54 of the second resilient member 50, which is spaced apart from the heater element 72. Therefore, the heater element 72 heats the medicament source 18 to a higher temperature than the volatile delivery enhancing compound source 22.

Figure 6:
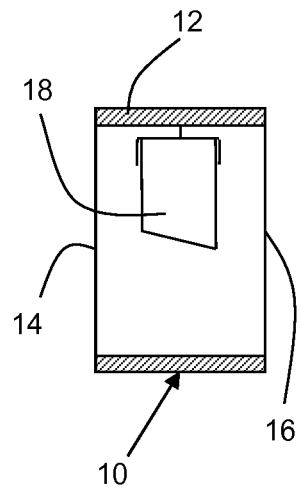
FIG. 6 shows a first consumable portion of an aerosol-generating article in accordance with a second embodiment of the present invention.

FIG. 6 shows a first consumable portion 10 of an aerosol-generating article according to a second embodiment of the present invention. The first consumable portion 10 is identical to the first consumable portion described above with respect to FIG. 1 and comprises a tubular segment 12 sealed at both ends by frangible barriers 14 and 16, and the medicament source 18 mounted on an inner surface of the tubular segment 12.

Figure 7:
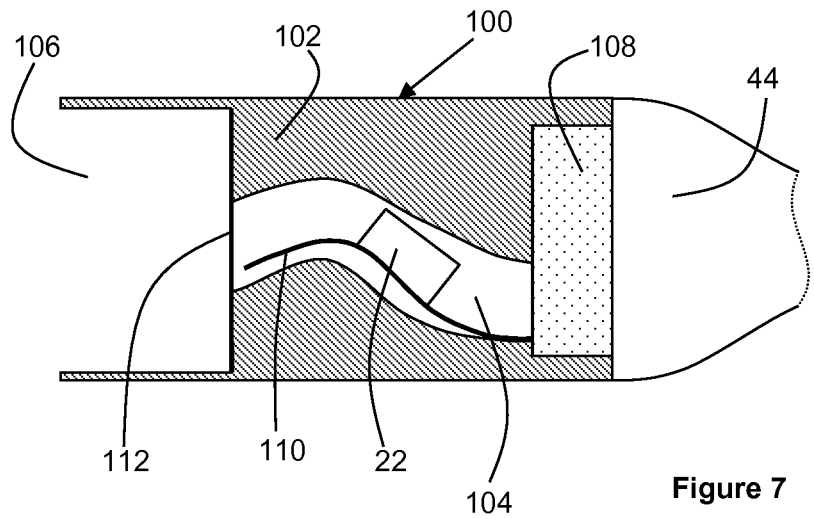
FIG. 7 shows a second consumable portion of an aerosol-generating article in accordance with the second embodiment of the present invention.

FIG. 7 shows a second consumable portion 100 of the aerosol-generating article according to the second embodiment of the invention. The second consumable portion comprises a housing 102 and a curved passage 104 formed inside the housing 102. The housing 102 is formed from a thermally insulating material, such as a plastic, and may be formed using a molding process to facilitate formation of the curved passage 104.

The housing 102 comprises a recess 106 for receiving the first consumable portion at an upstream end of the housing 102, and a mouthpiece 44 at the downstream end of the housing 102. As described previously, the mouthpiece may be formed integrally with the housing 102 or formed separately and attached to the housing 102. Optionally, the second consumable portion 100 may include a filter 108 at the downstream end of the housing 102, upstream of the mouthpiece 44. The filter may be formed from any suitable filter material known in the art, such as cellulose acetate.

A resilient member 110 is provided in the curved passage 104 and comprises a downstream end secured at the downstream end of the curved passage 104. As described previously, the resilient member 110 is formed from a thermally conductive resilient material, such as metal, capable of withstanding the operating temperature of the heater element that contacts the resilient member 110 during operation of the system.

A volatile delivery enhancing compound source 22, as described previously with respect to FIG. 1, is provided on the resilient member 110. A frangible barrier 112 seals the upstream end of the curved passageway 104. Preferably, a removable cover covers and seals the mouthpiece 44 to seal the downstream end of the second consumable portion 100.

Figure 8:
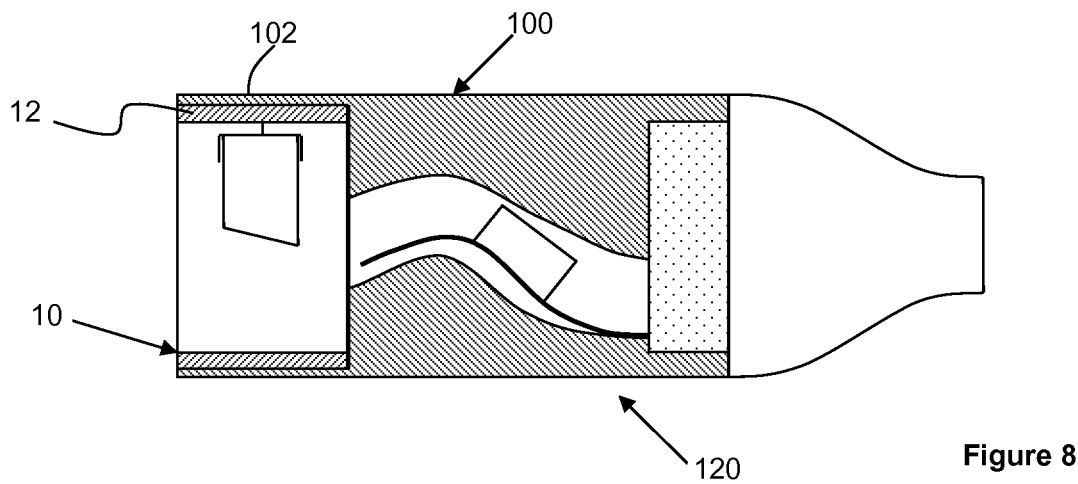
FIG. 8 shows the first and second consumable portions of FIGS. 6 and 7 combined to form an aerosol-generating article in accordance with the second embodiment of the present invention.

FIG. 8 shows the first consumable portion 10 inserted into the recess 106 of the second consumable portion 100 so that the first and second consumable portions 10 and 100 together form the aerosol-generating article 120 according to the second embodiment of the invention. The first consumable portion 10 is retained within the recess 106 by an interference fit between the tubular segment 12 and the housing 102.

Figure 9:
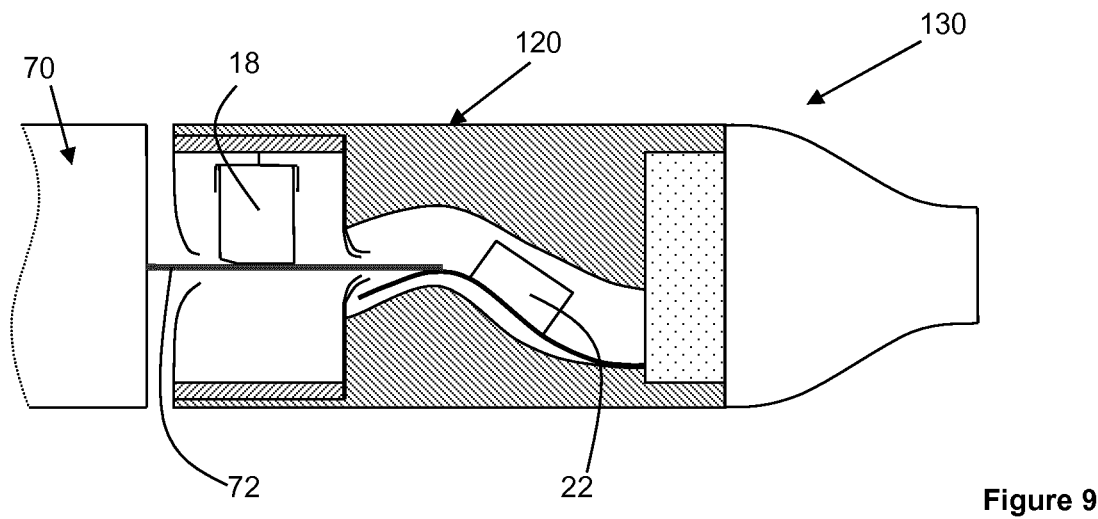
FIG. 9 shows an aerosol-generating device combined with the aerosol-generating article of FIG. 8 to form an aerosol-generating system in accordance with the second embodiment of the present invention.

FIG. 9 shows the aerosol-generating article 120 combined with the aerosol-generating device 70, described above, to form the aerosol-generating system 130 in accordance with the second embodiment of the present invention. Upon combining the aerosol-generating article 120 with the aerosol-generating device 70, the heater element 72 is inserted into the first consumable portion 10 and the upstream end of the curved passage 104. The heater element 42 functions as a piercing element so that insertion of the heater element 72 into the aerosol-generating article 120 ruptures the frangible barriers 14, 16 and 112 and allows air to flow into the upstream end of the aerosol-generating article 120, through the first consumable portion 10, the curved passage 104 and out of the downstream end of the aerosol-generating article 120 through the mouthpiece 44.

The downstream end of the heater element 72 contacts the upstream end of the resilient member 110 so that the resilient member 110 is resiliently biased against the heater element 72. During operation of the aerosol-generating system 130, the heater element 72 heats the medicament source 18 and the volatile delivery enhancing compound source 22. The medicament source 18 directly contacts the heater element 72, whereas the volatile delivery enhancing compound source 22 is heated via the resilient member 110. Therefore, the heater element 72 heats the medicament source 18 to a higher temperature than the volatile delivery enhancing compound source 22.

Figure 10:
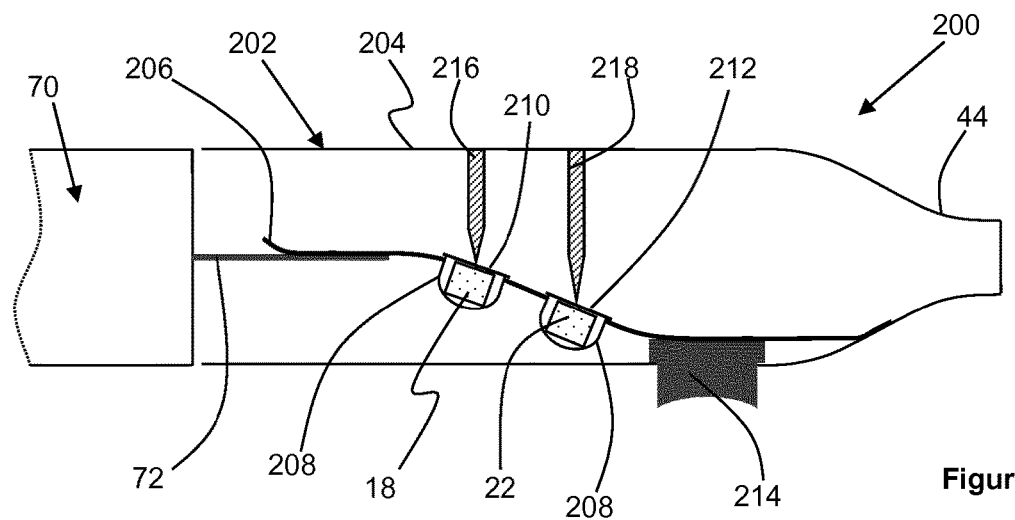
FIG. 10 shows an aerosol-generating system in accordance with a third embodiment of the present invention.

FIG. 10 shows an aerosol-generating system 200 in accordance with a third embodiment of the present invention. The aerosol-generating system comprises an aerosol-generating article 202 in combination with an aerosol-generating device 70, as described with respect to the previous embodiments.

The aerosol-generating article 202 comprises an outer housing 204 and a mouthpiece 44. As described previously, the mouthpiece 44 may be formed integrally with the outer housing 204, or the mouthpiece 44 may be formed separately. The outer housing 204 and the mouthpiece 44 are formed from a thermally insulating material, such as a plastic.

A medicament source 18 and a volatile delivery enhancing source 22, both as described previously, are provided on a resilient member 206. In the embodiment shown in FIG. 10, each of the medicament source 18 and the volatile delivery enhancing compound source 22 is provided in a recess 208 in the resilient member 206. However, the two sources could alternatively be provided on the surface of the resilient member 206. Frangible barriers 210 and 212 formed from a metal foil seal the medicament source 18 and the volatile delivery enhancing compound source 22 respectively. As described previously, the resilient member 206 is formed from a thermally conductive resilient material, such as metal, capable of withstanding the operating temperature of the heater element that contacts the resilient member 206 during operation of the system. With the heater element 72 of the aerosol-generating device 70 inserted into the aerosol-generating article 202, the heater element 72 contacts the upstream end of the resilient member 206 so that the resilient member 206 is resiliently biased against the heater element 72.

A downstream end of the resilient member 206 is secured to the outer housing 204 and a push-button 214 is attached to the resilient member 206. The push-button 214 extends through an aperture in the outer housing 204 so that the push-button 214 is accessible to a user. First and second piercing elements 216 and 218 extend from an inner surface of the outer housing 204 and overlie the medicament source 18 and the volatile delivery enhancing compound source 22 respectively. To activate the aerosol-generating article, a user pushes on the push-button 214 to deflect the resilient member 206 towards the first and second piercing elements 216 and 218 so that the first and second piercing element 216 and 218 pierce the frangible barriers 210 and 212. After releasing the push-button 204 the resilient member 206 returns to the pre-activation position so that the upstream end of the resilient member 206 is resiliently biased against the heater element 72.

During operation of the aerosol-generating system 200, the heater element 72 heats the medicament source 18 and the volatile delivery enhancing compound source 22 via the resilient member 206. The medicament source 18 is positioned on the resilient member 206 upstream from the volatile delivery enhancing compound source 22 and therefore closer to the heater element 72. Accordingly, the heater element 72 heats the medicament source 18 to a higher temperature than the volatile delivery enhancing compound source 22.

Figure 11:
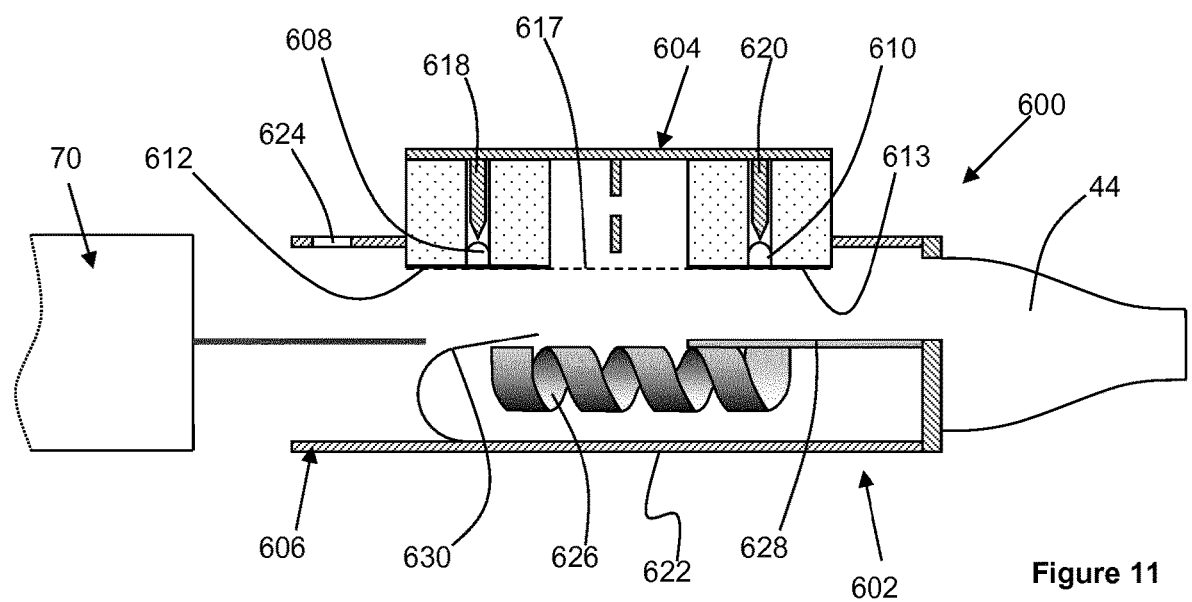
FIG. 11 shows an aerosol-generating system in accordance with a fourth embodiment of the present invention, before activation of the aerosol-generating article and before full insertion of the aerosol-generating device into the aerosol-generating article.
Figure 12:
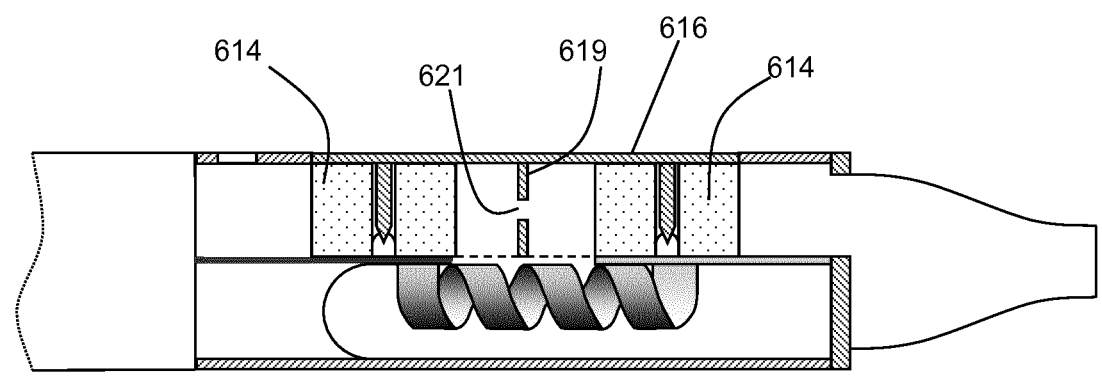
FIG. 12 shows the aerosol-generating system of FIG. 11 after activation of the aerosol-generating article and after full insertion of the aerosol-generating device into the aerosol-generating article.
Figure 13:
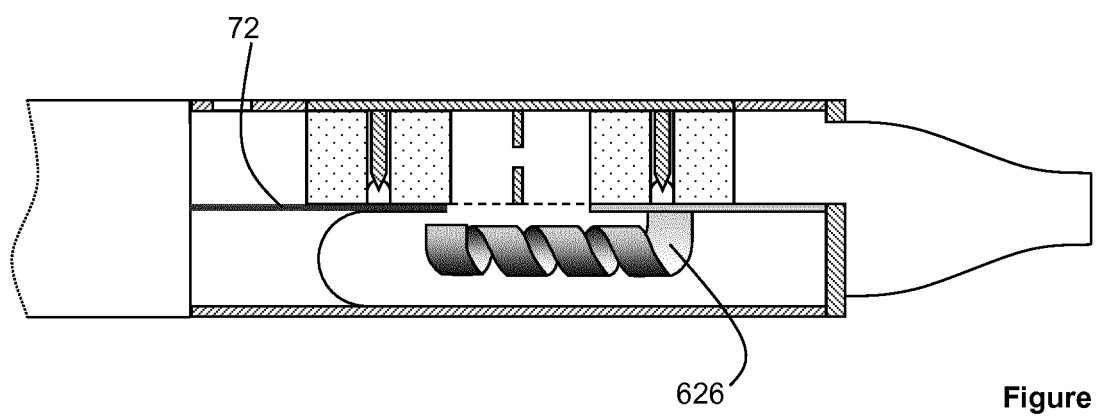
FIG. 13 shows the aerosol-generating system of FIG. 12 after the volatile delivery enhancing compound source has been heated to a predetermined temperature.

FIGS. 11, 12 and 13 show an aerosol-generating system 600 in accordance with a fourth embodiment of the present invention. The aerosol-generating system 600 comprises an aerosol-generating article 602 in combination with an aerosol-generating device 70, as described with respect to the previous embodiments.

The aerosol-generating article 602 comprises a consumable portion 604 and a reusable portion 606 that attaches to the aerosol-generating device 70. The consumable portion 604 comprises a medicament source in the form of a medicament blister 608 and a volatile delivery enhancing compound source in the form of a volatile delivery enhancing compound blister 610. The medicament blister 608 comprises a blister containing a liquid medicament, such as nicotine. The blister forms a frangible barrier sealing the medicament and is formed from a non-permeable material, such as a plastic. Similarly, the volatile delivery enhancing compound blister 610 comprises a blister containing a liquid volatile delivery enhancing compound. The blister forms a frangible barrier sealing the volatile delivery enhancing compound and is formed from a non-permeable material, such as a plastic.

The medicament blister 608 and the volatile delivery enhancing compound blister 610 are each mounted on a base plate 612 and 613 and each contained within a channel in a compressible sorption element 614. A top plate 616 overlies the sorption elements 614 and comprises side walls that extend downwardly and overlap similar side walls extending upwardly from each base plate 612 and 613. A captive mechanism, such as overlapping flanges on the side walls of the top plate 616 and each base plate 612 and 613, prevents the top plate 616 and the base plates 612 and 613 from becoming detached from each other. An overwrap 617 wraps around the top, sides and bottom of the consumable portion 604 to define an airflow passage between the upstream and downstream ends of the consumable portion 604.

First and second piercing elements 618 and 620 extend from an inner surface of the top plate 616 and overlie the medicament blister 608 and the volatile delivery enhancing compound blister 610 respectively. A restriction plate 619 comprising an airflow aperture 621 also extends from the inner surface of the top plate 616. To activate the consumable portion 604, a user depresses the top plate 616 towards the base plates 612 and 613 to compress the sorption elements 614 and to pierce the medicament blister 608 and the volatile delivery enhancing compound blister 610 with the first and second piercing elements 618 and 620. Upon piercing the blisters, the medicament and the volatile delivery enhancing compound are released and are at least partially sorbed onto the sorption elements 614.

To prevent accidental activation of the consumable portion 604, the consumable portion 604 may comprise one or more resilient biasing elements, such as one or more springs, positioned between the top plate 616 and the base plates 612 and 613 to bias the top plate 616 away from the base plates 612 and 613. Additionally, or alternatively, the consumable portion 604 may comprise one or more elements that function to retain the top plate 616 and the base plates 612 and 613 in the activated position after the consumable portion 604 has been activated. For example, an interference fit between a portion of the top plate 616 and a portion of each base plate 612 and 613 may retain the top plate 616 and the base plates 612 and 613 in the activated position after the consumable portion 604 has been activated.

The reusable portion 606 comprises an outer housing 622 and a mouthpiece 44 at a downstream end of the outer housing 622, as described previously. The mouthpiece 44 may be formed integrally with the outer housing 622, or the mouthpiece 44 may be formed separately and attached to the outer housing 622. An airflow inlet 624 at the upstream end of the outer housing 622 establishes an airflow passage through the outer housing 622 from the airflow inlet 624 to the mouthpiece 44.

A resilient member 626 comprises a thermally conductive element 628 extending from a downstream end of the housing and a bimetallic strip secured at its downstream end to the thermally conductive element 628. An upstream end of the bimetallic strip is resiliently biased against the heater element 72 of the aerosol-generating device 70 when the heater element 72 is inserted into the reusable portion 606, as shown in FIG. 21. To ensure correct and optimum contact between the heater element 72 and the upstream end of the bimetallic strip, a resilient contact spring 630 may be positioned adjacent the upstream end of the bimetallic strip. Although the bimetallic strip is illustrated as having a spiral shape, other shapes could also be used. For example, a simple flat bimetallic strip can be attached at its downstream end to the thermally conductive element 628 to form a bimetallic cantilever.

To prepare the aerosol-generating system 600 for operation, the consumable portion 604 is inserted into the reusable portion 606 through an aperture in a sidewall of the outer housing 622. Pushing the consumable portion 604 into the reusable portion 606 brings the base plate 612 into contact with the heater element 72 and brings the base plate 613 into contact with the thermally conductive element 628, as shown in FIG. 12. The consumable portion 604 may be pre-activated by the user, or the action of pushing the consumable portion 604 into the reusable portion may activate the consumable portion 604.

During operation of the aerosol-generating system 600, the heater element 72 heats the medicament source via the base plate 612 and heats the volatile delivery enhancing compound source via the resilient member 626 in the form of the bimetallic strip, the thermally conductive element 628 and the base plate 613. For this reason, the base plates 612 and 613 are constructed from a thermally conductive material, such as a metal. The bimetallic strip is configured, through appropriate choice of the metals forming the strip and the shape of the strip, to undergo mechanical displacement of the upstream end of the bimetallic strip away from the heater element 72 when a predetermined temperature is reached, as shown in FIG. 13. Once the predetermined temperature is reached, the upstream end of the bimetallic strip no longer contacts the heater element 72, so that the volatile delivery enhancing compound source is no longer heated. As the bimetallic strip cools again it returns to its pre-heating shape and position so that its upstream end re-contacts the heater element 72. In this way, the bimetallic strip provides thermostatic control of the heating of the volatile delivery enhancing compound source. By appropriate selection of the predetermined temperature at which the switching of the bimetallic strip occurs, the heater element 72 heats the medicament source to a higher temperature than the volatile delivery enhancing compound source.

FIGS. 14 and 15 show an aerosol-generating system 700 according to a fifth embodiment of the present invention. The aerosol-generating system 700 comprises an aerosol-generating article 702 in combination with an aerosol-generating device 70, as described previously.

The aerosol generating article 702 comprising a first tubular segment 704, a second tubular segment 706 and a third tubular segment 708, all received within a tubular outer housing 710. The first tubular segment 704 is fixed within the outer housing 710, and the second and third tubular segments 706 and 708 are slidably received within the outer housing 710.

A first sorption element 712 is mounted within the first tubular segment 704 and comprises an upstream face and a downstream face. First and second resilient members 714 and 716 are provided on the upstream face of the first sorption element 712 and are positioned adjacent each other to receive the heater element 72 of the aerosol-generating device 70 between them. When the heater element 72 is inserted into the aerosol-generating article 702, as shown in FIG. 24, the first and second resilient members 714 and 716 are resiliently biased against the heater element 72 so that they grip the heater element 72.

As described with respect to previous embodiments, the resilient members 714 and 716 are formed from a thermally conductive resilient material, such as metal, capable of withstanding the operating temperature of the heater element. In the embodiment shown in FIG. 14, the first and second resilient members 714 and 716 are formed from a single piece of resilient material so that the downstream ends of the resilient members are connected by a continuous portion of the resilient material. However, the first and second resilient members 714 and 716 can alternatively be formed separately and separately mounted on the first sorption element 712.

Depending on the material used to form the first sorption element 712, it may be preferably to provide an intermediate mounting plate formed from a rigid thermally conductive material between the first sorption element 712 and the resilient members 714 and 716.

A medicament source in the form of a medicament blister 718 is provided on the downstream face of the first sorption element 712. The medicament blister comprises a liquid medicament contained within a blister, as described with respect to the previous embodiment. The blister forms a frangible barrier containing the liquid medicament.

The second tubular segment 706 comprises a divider plate 720 mounted within the second tubular segment 706. A first piercing element 722 extends from the upstream face of the divider plate 720 and a second piercing element 724 extends from the downstream face of the divider plate 720.

The third tubular segment 708 comprises a second sorption element 726 mounted within the first tubular segment 704 and comprising an upstream face and a downstream face. A volatile delivery enhancing compound source in the form of a volatile delivery enhancing compound blister 728 is provided on the upstream face of the second sorption element 726 and comprises a liquid volatile delivery enhancing compound contained within a blister, as described with respect to the previous embodiment. The blister forms a frangible barrier containing the liquid volatile delivery enhancing compound. A mouthpiece 44, as described previously, extends downstream from the third tubular segment 708.

The aerosol-generating device 702 also comprises airflow inlets 730 in the outer housing 710 upstream of the first tubular segment 704, and an annular stopper 732 provided on an inner surface of the outer housing 710 upstream of the first and second resilient members 714 and 716. The aerosol-generating device 70 is inserted into the aerosol-generating article 702 until the aerosol-generating device 70 abuts the annular stopper 732, as shown in FIG. 23.

To activate the aerosol-generating article 702, a user pushes the third tubular segment 708 into the outer housing 710 so that the third tubular segment 708 pushes the second tubular segment 706 towards the first tubular segment 704. The user continues to push the third tubular segment 708 until the second tubular segment 706 abuts the first tubular segment 704 and the third tubular segment 708 abuts the second tubular segment 706, as shown in FIG. 24. Pushing the three tubular segments together causes the first and second piercing elements 722 and 724 to pierce the medicament blister 718 and the volatile delivery enhancing compound blister 728, which releases the liquid medicament and the liquid volatile delivery enhancing compound onto the respective sorption elements.

During operation of the aerosol-generating system 700, the heater element 72 heats the medicament source via the first and second resilient members 714 and 716. The volatile delivery enhancing compound source, which is positioned further downstream, is heated via the first and second resilient members 714 and 716, and the first, second and third tubular segments 704, 706 and 708. Therefore, the heater element 72 heats the medicament source to a higher temperature than the volatile delivery enhancing compound source.

The invention claimed is:

1. An aerosol-generating system, comprising:
    an aerosol-generating device comprising a heater element; and
    an aerosol-generating article configured to engage with the aerosol-generating device and comprising:
        a medicament source;
        a volatile delivery enhancing compound source;
        a tubular portion housing the medicament source and the volatile delivery enhancing compound source;
        at least one frangible barrier extending across at least one end of the tubular portion and sealing the medicament source and the volatile delivery enhancing compound source; and
        a mouthpiece portion housing at least one piercing element and being configured to receive the tubular portion within the mouthpiece portion,
        wherein the at least one piercing element comprises at least one resilient member configured to pierce the at least one frangible barrier when the tubular portion is inserted into the mouthpiece portion,
    wherein the heater element is an elongate heater element comprising a proximal end attached to the aerosol-generating device and a free distal end configured to be inserted into the aerosol-generating article, and
    wherein the at least one resilient member is configured such that the at least one resilient member is resiliently biased against the heater element when the aerosol-generating article is engaged with the aerosol-generating device.

2. The aerosol-generating system according to claim 1, wherein the at least one resilient member comprises first and second resilient members configured such that each resilient member is resiliently biased against the heater element when the aerosol-generating article is engaged with the aerosol-generating device so that the heater element is positioned between the first and second resilient members.

3. The aerosol-generating system according to claim 1, wherein the aerosol-generating device and the aerosol-generating article are configured to heat the medicament source to a temperature of between 50 degrees Celsius and 150 degrees Celsius.

4. The aerosol-generating system according to claim 1, wherein the aerosol-generating device and the aerosol-generating article are configured to heat the volatile delivery enhancing compound source to a temperature of between 30 degrees Celsius and 100 degrees Celsius.

5. The aerosol-generating system according to claim 1, wherein the medicament source comprises a nicotine source.

6. The aerosol-generating system according to claim 1, wherein the volatile delivery enhancing compound source comprises an acid.

* * * * *